US010980990B1

(12) United States Patent
Jackson

(10) Patent No.: US 10,980,990 B1
(45) Date of Patent: *Apr. 20, 2021

(54) SYSTEMS, DEVICES, AND/OR METHODS FOR MANAGING TRANSDERMAL PATCHES

(71) Applicant: N Brereton Medical Technologies, LLC, Forest, VA (US)

(72) Inventor: Neil Brereton Jackson, Forest, VA (US)

(73) Assignee: N Brereton Medical Technologies, LLC, Forest, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/068,069

(22) Filed: Oct. 12, 2020

Related U.S. Application Data

(63) Continuation of application No. 16/853,819, filed on Apr. 21, 2020, now Pat. No. 10,842,980, which is a continuation of application No. 16/540,132, filed on Aug. 14, 2019, now Pat. No. 10,661,065.

(60) Provisional application No. 62/802,288, filed on Feb. 7, 2019.

(51) Int. Cl.
*A61M 35/00* (2006.01)
*A61F 13/00* (2006.01)
*A61M 31/00* (2006.01)
*A61M 37/00* (2006.01)
*A61K 9/70* (2006.01)

(52) U.S. Cl.
CPC ... *A61M 35/10* (2019.05); *A61F 2013/00646* (2013.01); *A61F 2013/00906* (2013.01); *A61K 9/7023* (2013.01); *A61K 9/7084* (2013.01); *A61M 31/002* (2013.01); *A61M 37/00* (2013.01); *A61M 2205/3334* (2013.01)

(58) Field of Classification Search
CPC ... A61K 9/7084; A61K 9/7023; A61M 35/10; A61M 2205/3334; A61M 31/002; A61M 37/00; Y10S 514/947; A61F 2013/00646; A61F 2013/00906
USPC ........................................................ 604/307
See application file for complete search history.

(56) References Cited

U.S. PATENT DOCUMENTS

| | | | | |
|---|---|---|---|---|
| 4,597,961 A * | 7/1986 | Etscorn | ............... | A61K 9/7084 424/448 |
| 4,624,665 A * | 11/1986 | Nuwayser | ............ | A61K 9/7084 424/448 |
| 8,691,268 B2 * | 4/2014 | Weimann | ............. | A61K 9/0009 424/449 |
| 10,661,065 B1 * | 5/2020 | Jackson | ................ | A61M 35/00 |
| 10,842,980 B1 * | 11/2020 | Jackson | ................ | A61M 35/00 |
| 2008/0097282 A1 * | 4/2008 | Hole | .................... | A61K 9/7007 604/23 |
| 2013/0060209 A1 * | 3/2013 | Tyler | ................ | A61F 13/00063 604/307 |

(Continued)

*Primary Examiner* — Andrew J Mensh
(74) *Attorney, Agent, or Firm* — Michael Haynes PLC; Michael N. Haynes

(57) ABSTRACT

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, controlling delivery of a transdermally-delivered medication, certain embodiments including a flux controller.

20 Claims, 12 Drawing Sheets

(56) References Cited

U.S. PATENT DOCUMENTS

2013/0317461 A1* 11/2013 Kanios ................. A61K 9/7061
604/307
2014/0276478 A1* 9/2014 Liao ....................... A61K 31/13
604/290

* cited by examiner

1000

SYSTEMS, DEVICES, AND/OR METHODS FOR MANAGING TRANSDERMAL PATCHES

CROSS-REFERENCES TO RELATED APPLICATIONS

This application claims priority to, and incorporates by reference herein in its entirety, U.S. Provisional Patent Application 62/802,288, filed 7 Feb. 2019.

BRIEF DESCRIPTION OF THE DRAWINGS

A wide variety of potential, feasible, and/or useful embodiments will be more readily understood through the herein-provided, non-limiting, non-exhaustive description of certain exemplary embodiments, with reference to the accompanying exemplary drawings in which.

DESCRIPTION

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, controlling delivery of a transdermally-delivered medication, certain embodiments including a flux controller.

Referring to FIGS. 1-12, certain exemplary embodiments from a wide variety of possible embodiments of system 1000 can comprise a flux controller (also referred to herein as a "barrier") 1200 that is positioned and/or configured to be positioned between a delivery face 1170 of a transdermal patch 1100 and the outer layer of skin (i.e., epidermis and/or stratum corneum) 1300 of a subject to be treated with a medication that is transdermally-delivered from delivery face 1170 of patch 1100 to the subject. Barrier 1200 can be configured to manage, control, direct, channel, block, impede, reduce, and/or slow a flux or flow of the medication from a corresponding portion of delivery face 1170 to skin 1300, thereby providing, over a given interval of time, a lower dose of the medication than would occur without barrier 1200 in place.

Figure 1:
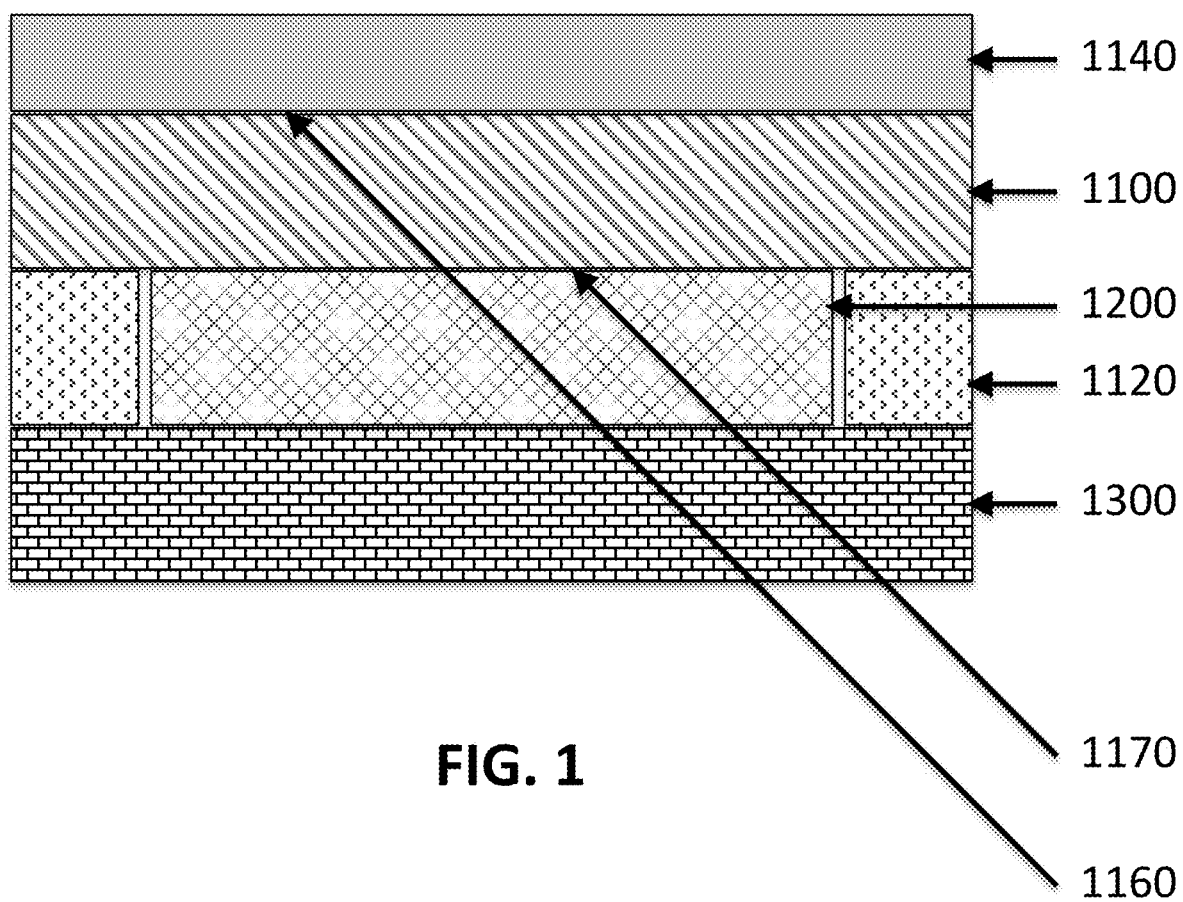
FIG. 1 is an edge view of an exemplary embodiment of a system.

FIG. 1 is an edge view of an exemplary embodiment of system 1000, showing an impermeable backing 1140 that can be adhered to a back face 1160 of patch 1100. Barrier 1200 can be positioned between delivery face 1170 of patch 1100 and skin 1300. Patch 1100 can be adhered to skin 1300 by adhesive 1120.

Figure 2:
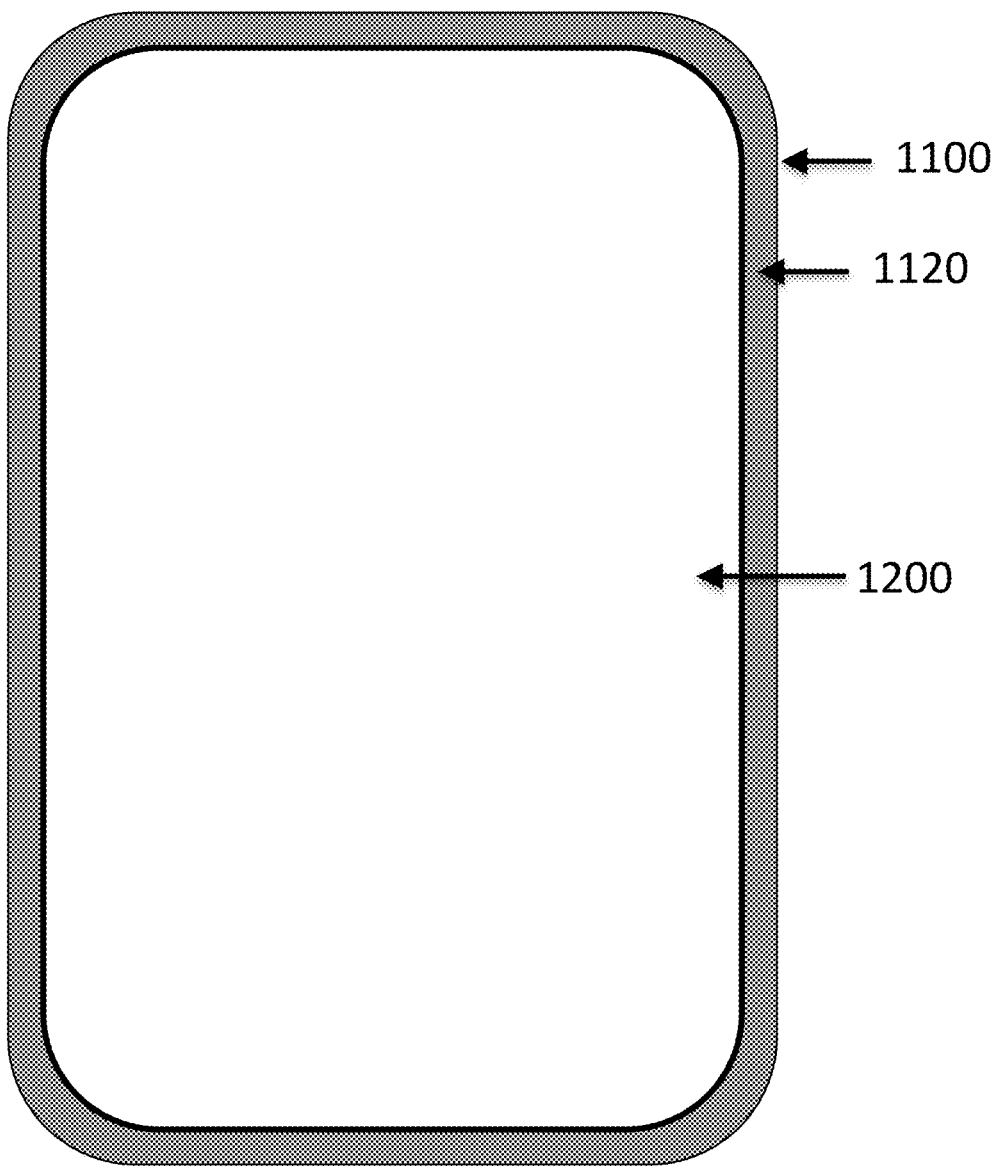
FIG. 2 is a side view of an exemplary embodiment of a system.

FIG. 2 is a side view of an exemplary embodiment of system 1000, showing patch 1100, adhesive 1120, and barrier 1200 (covering most of patch 1100).

Figure 3:
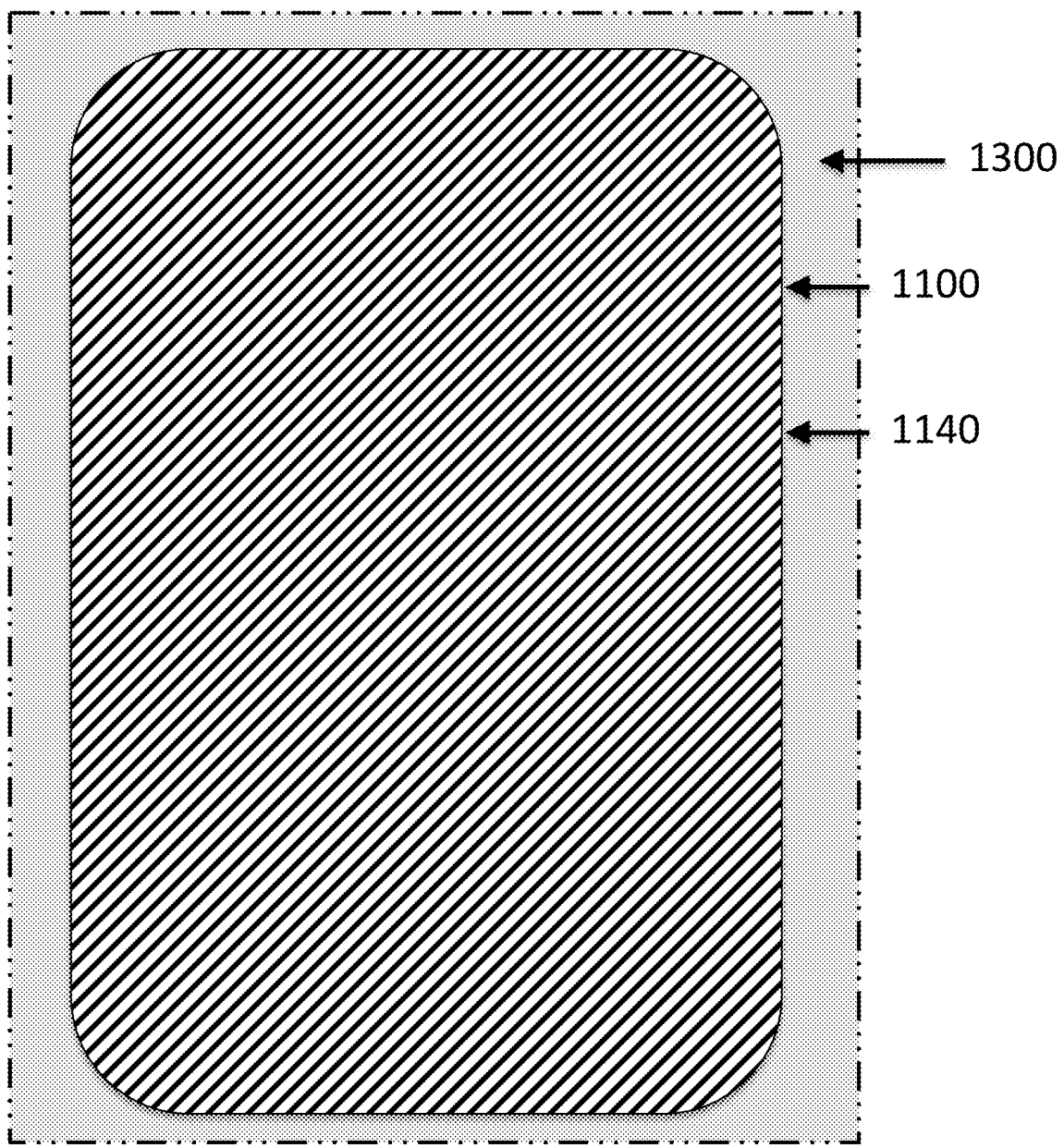
FIG. 3 is a side view of an exemplary embodiment of a system.

FIG. 3 is a side view of an exemplary embodiment of system 1000, showing impermeable backing 1140 adhered to and completely covering patch 1100, which is applied to skin 1300.

Figure 4:
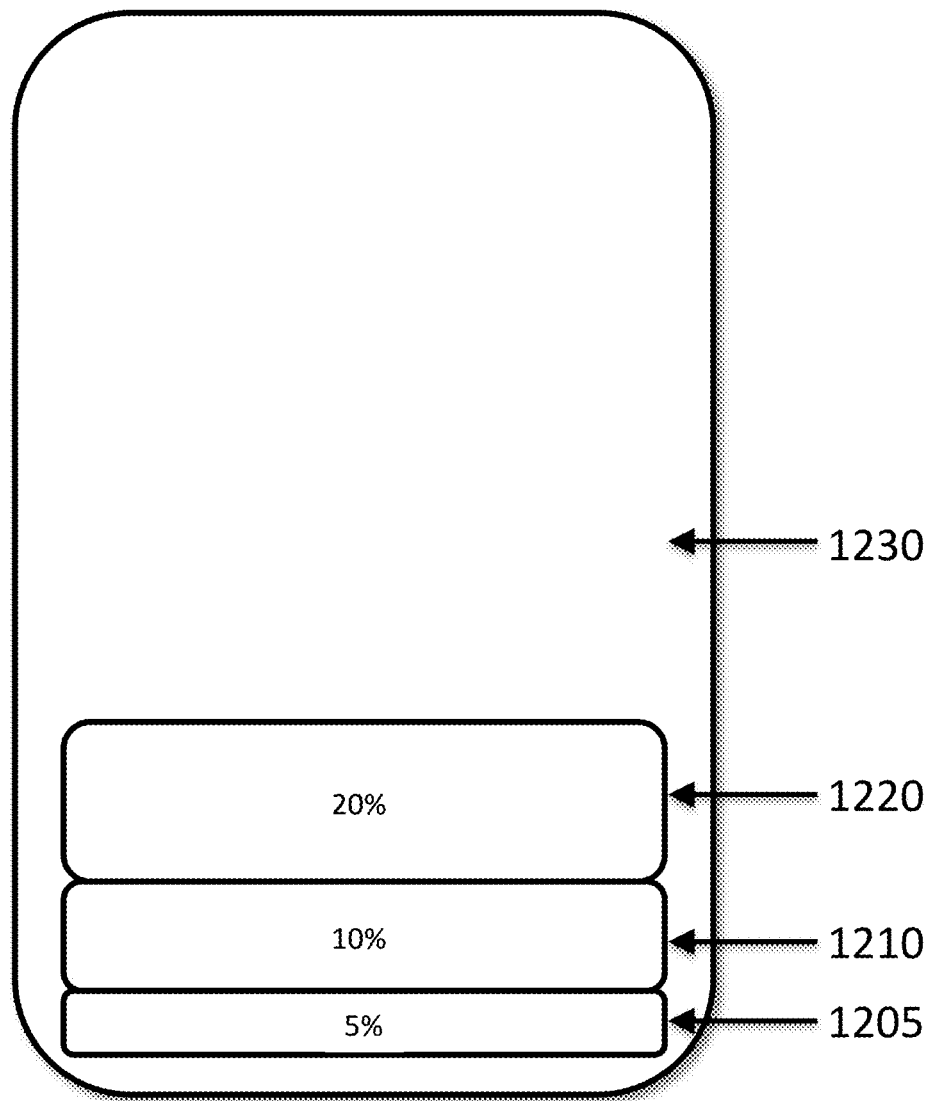
FIG. 4 is a side view of an exemplary embodiment of a system.

FIG. 4 is a side view of an exemplary embodiment of system 1000, showing a barrier sheet 1230 that is formed from barrier material. Also shown are substantially rectangular pre-cut and/or perforated shaped barriers 1220, 1210, and 1205, each of which can be separated from barrier sheet 1230 and/or each other to define all or a portion of a barrier 1200. Shaped barrier 1220 can be sized and/or configured to control, block, impede, reduce, and/or slow a flow or flux of the medication from a corresponding portion of delivery face 1170 of patch 1100 to skin 1300. For example, by covering 20 percent of delivery face 1170, shaped barrier 1220 can be configured to control, block, impede, reduce, and/or slow 20 percent of the labeled and/or designed flow from patch 1100 to skin 1300. A table (paper and/or software app) can be provided for looking-up a given manufacturer, medication, and dosage to determine what size and/or shape of shaped barrier to select to achieve a desired reduction in the labeled and/or designed flow from patch 1100 to skin 1300.

Figure 5:
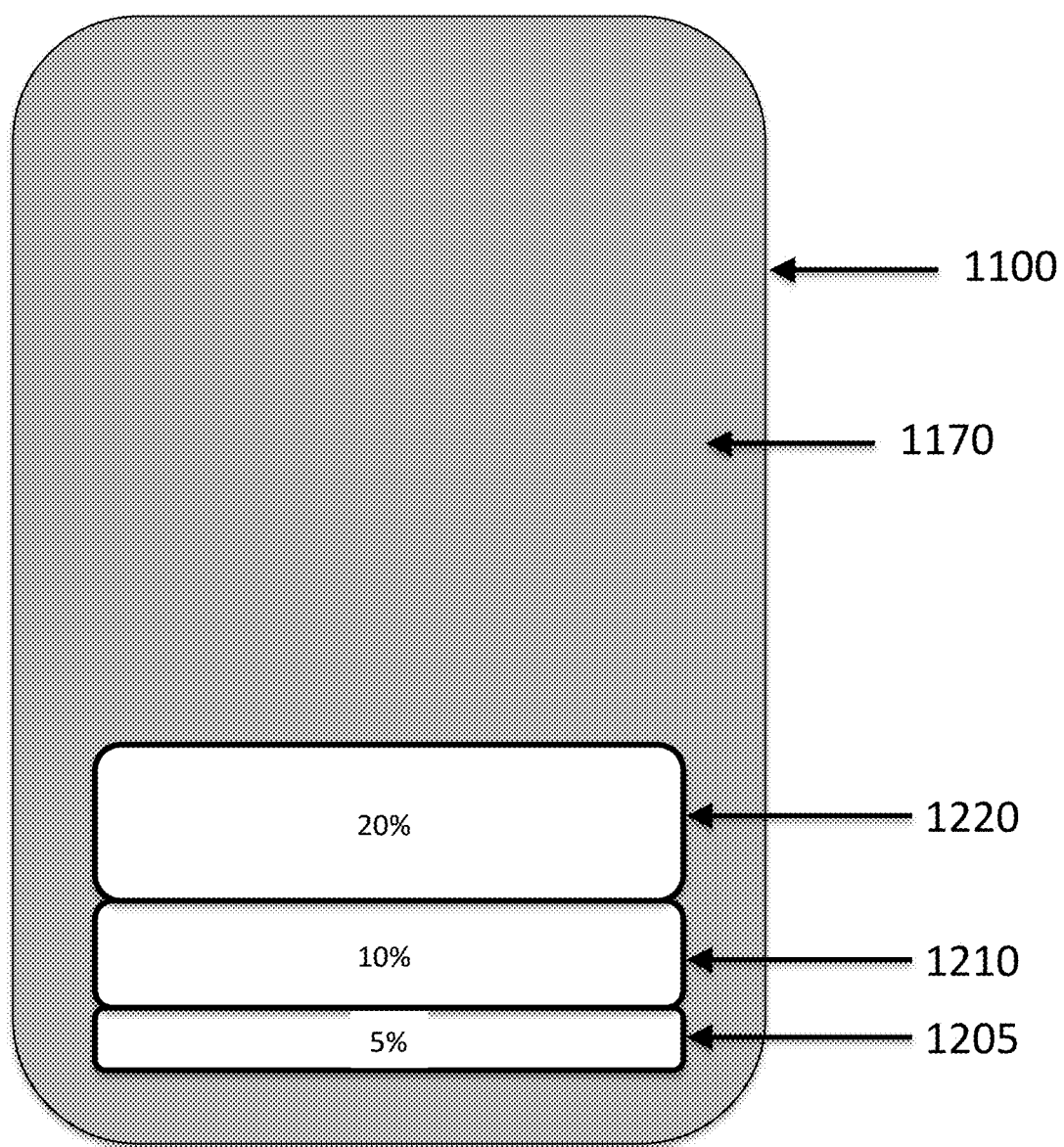
FIG. 5 is a side view of an exemplary embodiment of a system.

FIG. 5 is a side view of an exemplary embodiment of system 1000, showing shaped barriers 1220, 1210, and 1205, as removed from the reminder of a barrier sheet 1230 (see FIG. 4), and as positioned on delivery face 1170 to control, block, impede, reduce, and/or slow a medication flow from patch 1100 to skin 1300. For example, shaped barriers 1220, 1210, and 1205 can be configured to collectively cover a portion (e.g., 35 percent) of delivery face 1170, while a portion (e.g., 65 percent) of delivery face 1170 remains uncovered by barrier material. Likewise, shaped barriers 1220, 1210, and 1205 can be configured to collectively control, block, impede, reduce, and/or slow a portion (e.g., 35 percent) of the labeled and/or designed medication flow while a portion (e.g., 65 percent) of the medication flow is unimpeded by barrier material, and thus the patient receives only 65 percent of the labeled and/or designed medication flowrate.

Figure 6:
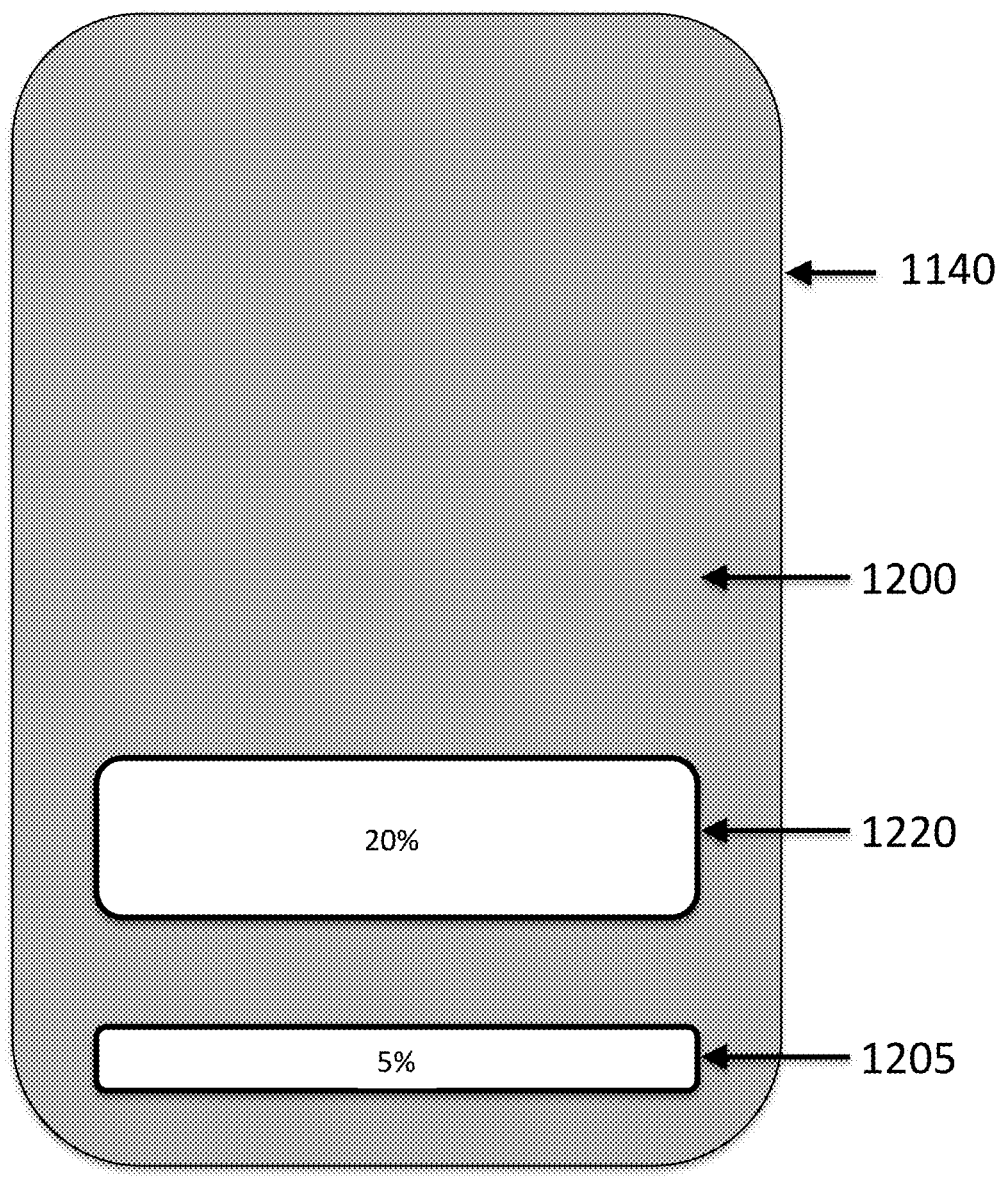
FIG. 6 is a side view of an exemplary embodiment of a system.

FIG. 6 is a side view of an exemplary embodiment of system 1000, showing shaped barriers 1220 and 1205 positioned on delivery face 1170 to control, block, impede, reduce, and/or slow the medication flow from patch 1100 to skin 1300. In this example, because fewer shaped barriers are present, a smaller portion of medication (e.g., 25 percent) can be controlled, blocked, impeded, reduced, and/or slowed from flowing from patch 1100 to skin 1300, while a larger portion (e.g., 75 percent) of delivery face 1170 is uncovered by barrier material and thus a larger portion (e.g., 75 percent) of medication can flow as designed from patch 1100 to skin 1300.

Figure 7:
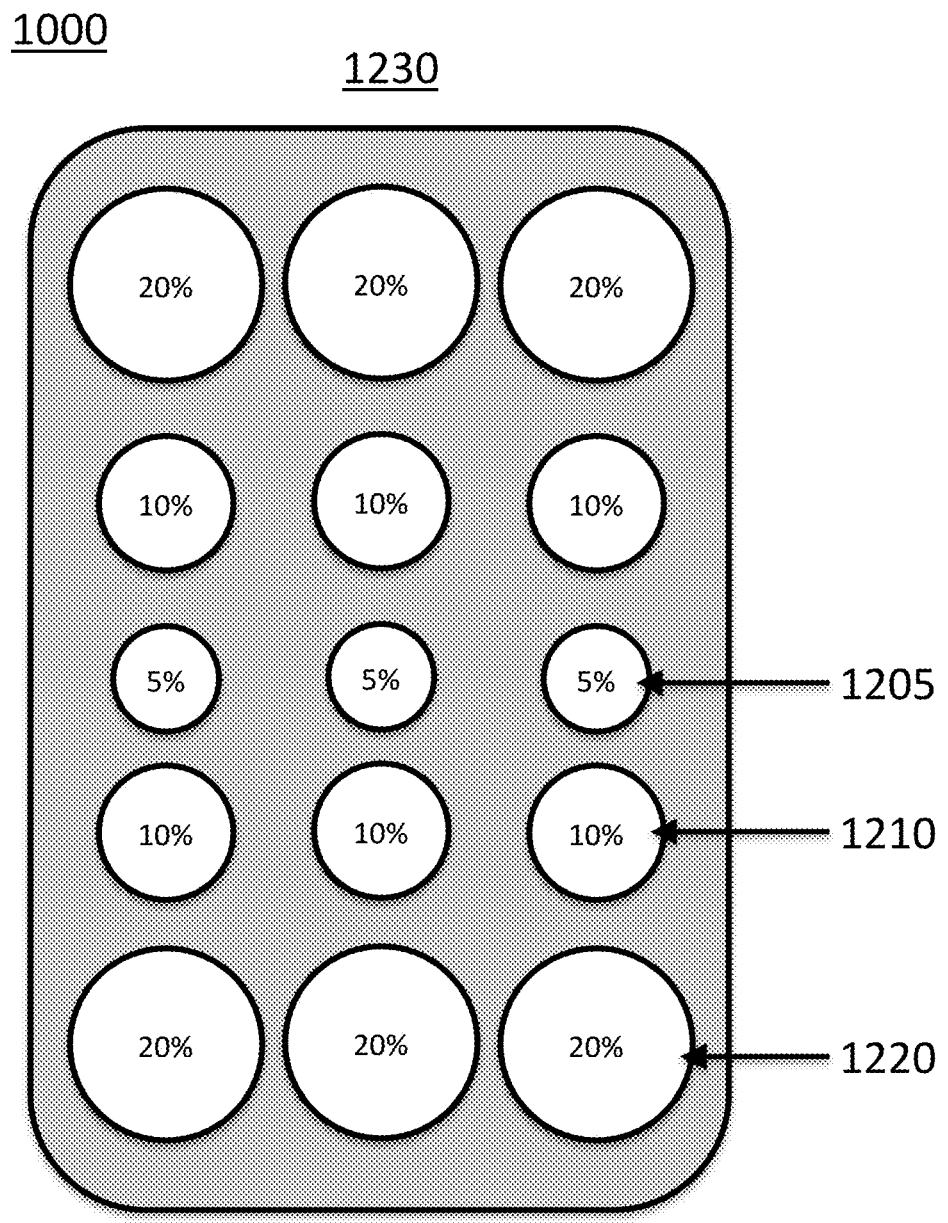
FIG. 7 is a side view of an exemplary embodiment of a system.

FIG. 7 is a side view of an exemplary embodiment of system 1000, showing barrier sheet 1230. Also shown are multiple instances of substantially circular pre-cut and/or perforated shaped barriers, e.g., 1220, 1210, and 1205, each of which can define a corresponding portion of barrier sheet 1230, and/or each of which can define all or a portion of a barrier 1200.

As an example, shaped barrier 1220 can be sized and/or configured to control, block, impede, reduce, and/or slow a flow or flux of the medication from a corresponding portion of patch 1100 to skin 1300. For example, by covering 20 percent of delivery face 1170, shaped barrier 1220 can be configured to block 20 percent of the labeled and/or designed flow from patch 1100 to skin 1300.

Figure 8:
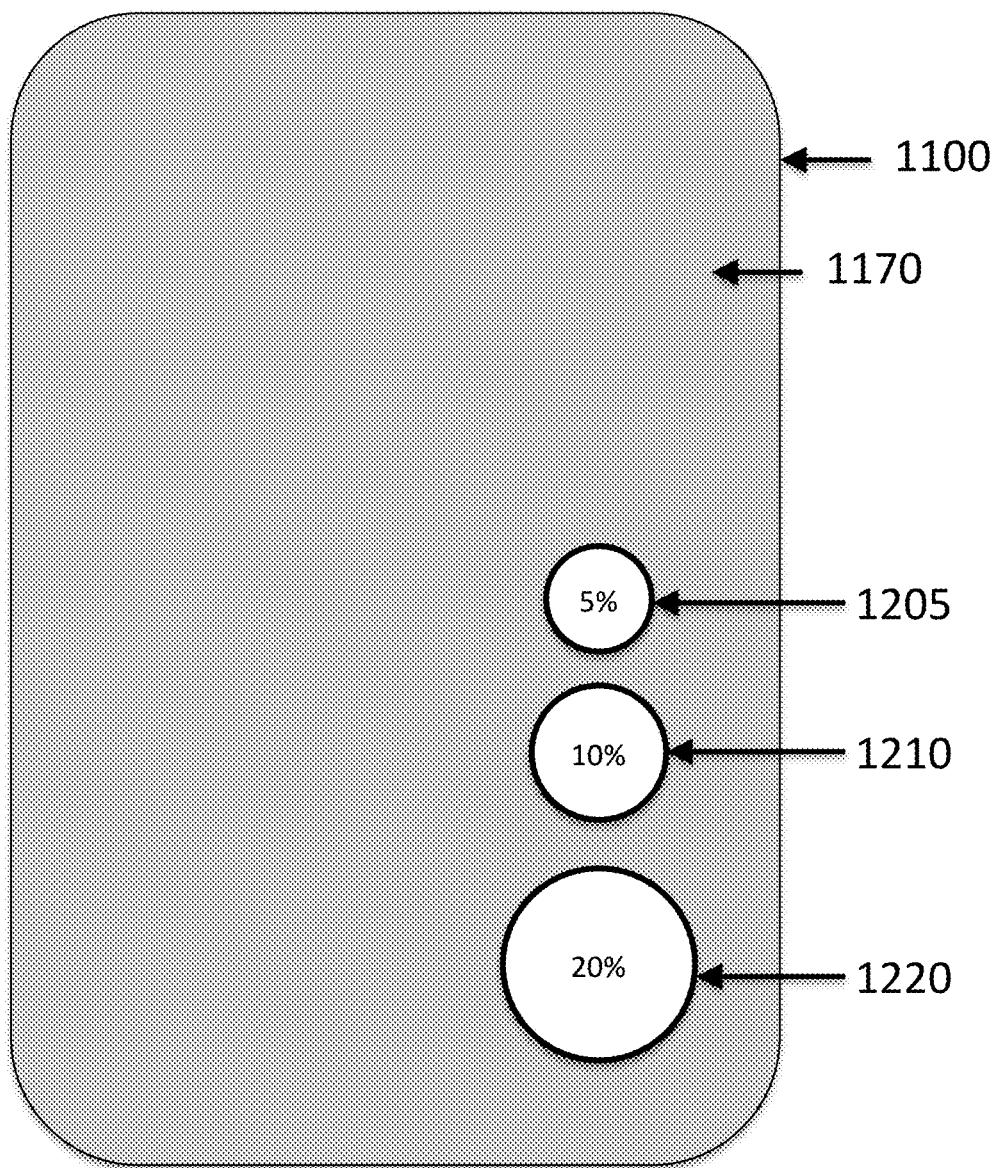
FIG. 8 is a side view of an exemplary embodiment of a system.

FIG. 8 is a side view of an exemplary embodiment of system 1000, showing shaped barriers 1220, 1210, and 1205 positioned on and/or adjacent delivery face 1170 to block and/or control a medication flow from patch 1100. For example, shaped barriers 1220, 1210, and 1205 can be configured to collectively cover a portion (e.g., 35 percent) of delivery face 1170 while a portion (e.g., 65 percent) of delivery face 1170 is uncovered by barrier material. Likewise, shaped barriers 1220, 1210, and 1205 can be configured to collectively control, block, impede, and/or slow a portion (e.g., 35 percent) of the labeled and/or designed medication flux and/or flow while a portion (e.g., 65 percent) of the medication flux and/or flow is uncontrolled and/or unimpeded by barrier material, and thus the patient receives only 65 percent of the medication.

Figure 9:
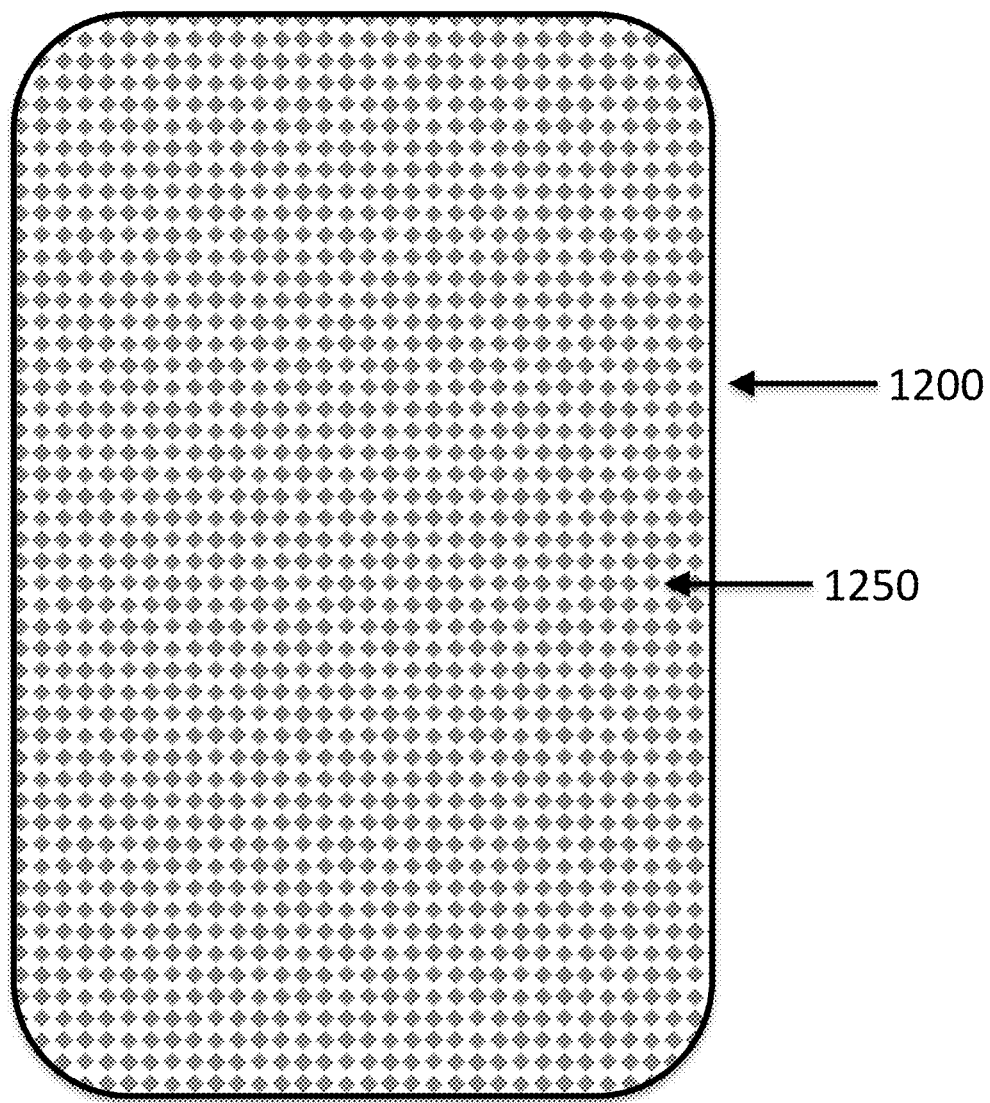
FIG. 9 is a side view of an exemplary embodiment of a system.

FIG. 9 is a side view of an exemplary embodiment of system 1000, showing barrier 1200. In this embodiment, barrier 1200 defines a plurality of apertures 1250 therethrough, the apertures 1250 configured to allow a portion of the medication to pass therethrough to the skin. For example, barrier 1200 can be configured as a semi-permeable or permeable barrier material, such as a layer, film, foil, and/or tape that can be positioned to cover all or a portion of unshown delivery face 1170. Apertures 1250 can be uniformly and/or non-uniformly distributed across barrier material in a random, predetermined, and/or arrayed pattern. Apertures 1250 can be uniformly and/or non-uniformly sized and/or dimensioned (e.g., diameter and/or average width).

Figure 10:
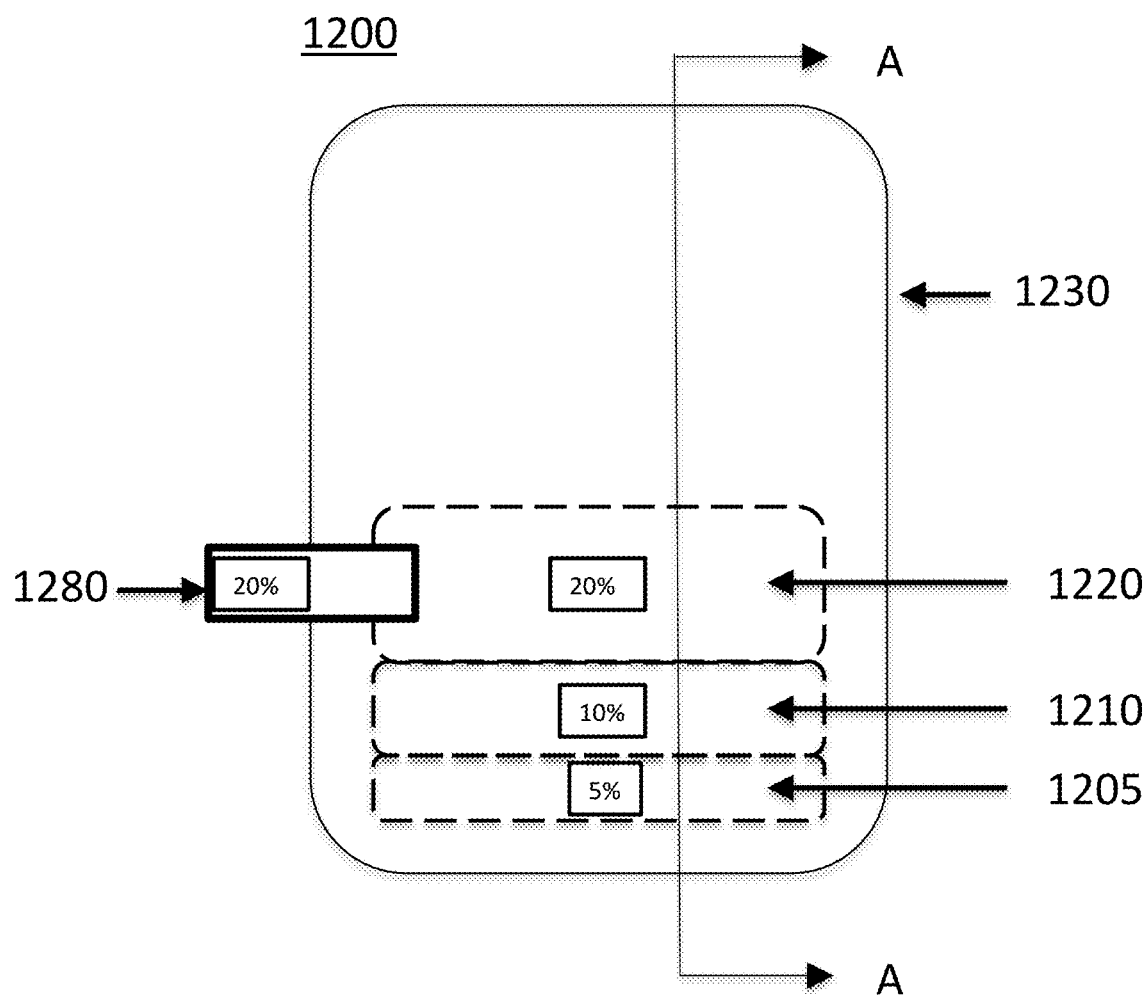
FIG. 10 is a side view of an exemplary embodiment of a system.

FIG. 10 is a side view of an exemplary embodiment of system 1000, showing a barrier sheet 1230 that is formed from barrier material. Also shown are substantially rectangular pre-cut and/or perforated shaped barriers 1220, 1210, and 1205, each of which can be separated from barrier sheet 1230 and/or each other to define all or a portion of a barrier 1200. Shaped barriers 1220, 1210, and/or 1205 can be labeled to indicate their flow control capability. As shown in this example, shaped barrier 1220 has a tab 1280 that is labeled, while shaped barrier 1210 and 1205 are directly labeled.

Figure 11:
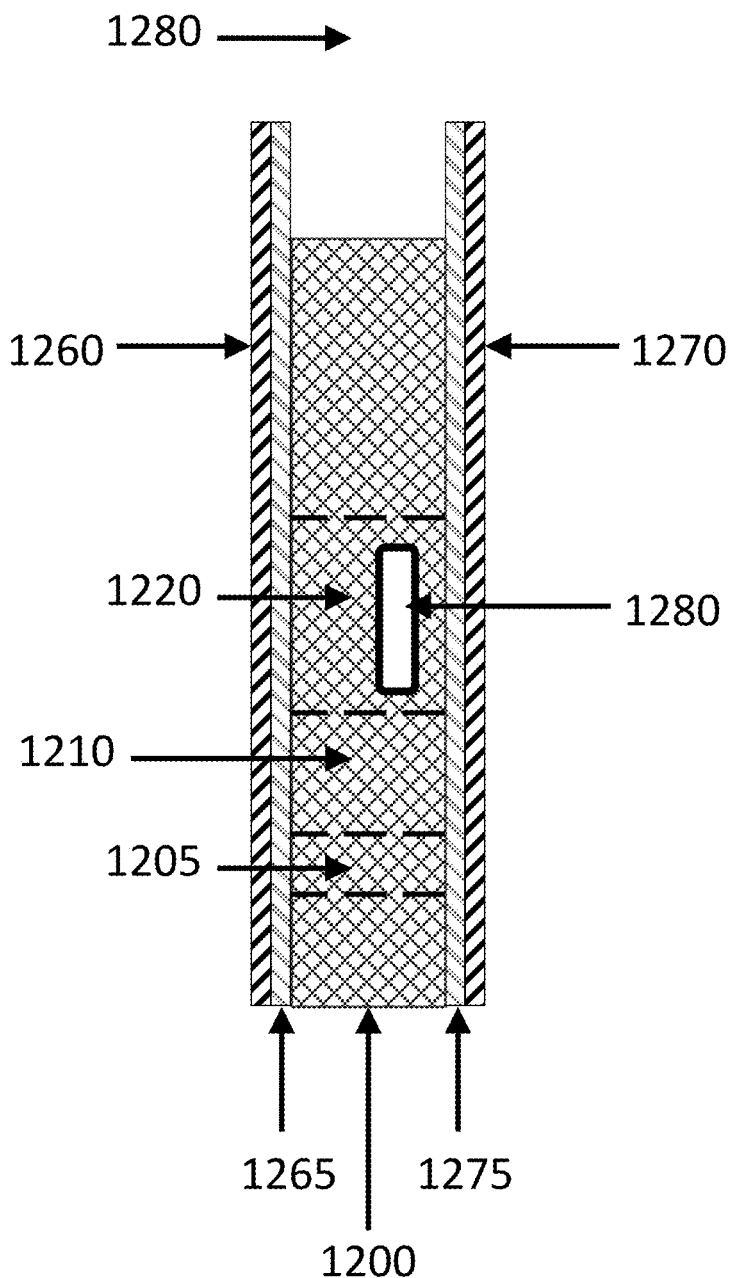
FIG. 11 is a section view of an exemplary embodiment of a system.

FIG. 11 is a cross-sectional view, taken at section A-A of FIG. 10, of an exemplary embodiment of system 1000, showing a barrier 1200 having a first barrier backing 1260 and a second barrier backing 1270. Either of barrier backings 1260 and 1270 can be removed from barrier 1200 as needed to apply barrier 1200 to unshown patch 1100 or skin 1300. Barrier 1200 can be supplied with a first adhesive layer 1265 that attaches it to first barrier backing 1260 and/or allows barrier 1200 to be attached to unshown patch 1100 or skin 1300. Likewise, barrier 1200 can be supplied with a second adhesive layer 1275 that attaches it to second barrier backing 1270 and/or allows it to be attached to unshown patch 1100 or skin 1300. Alternatively, barrier 1200 can be unattached to or attached by other mechanisms, such as interconnections between shaped barriers and/or static charge, to first barrier backing 1260 and/or second barrier backing 1270.

The barrier material can have a predetermined (e.g., 50, 70, 75.2, 80, 84.93, 90, or 95, etc. percent (including all real number values and subranges therebetween)) medication impermeability, and thus the barrier material would control, block, impede, reduce, and/or slow a portion (e.g., 50, 70, 75.2, 80, 84.93, 90, or 95, etc. percent (including all real number values and subranges therebetween)) of the labeled and/or designed flow of medication from patch 1100 to skin 1300. The barrier material can be configured function as a barrier for at least the life of the patch and/or can have properties sufficient to control, block, impede, reduce, and/or slow a portion (e.g., 50, 70, 75.2, 80, 84.93, 90, or 95, etc. percent (including all real number values and subranges therebetween)) of the labeled and/or designed flow of medication from patch 1100 to skin 1300, such as being non-dissolving, tear-resistant, child-resistant, puncture-resistant, fold-resistant, chemically resistant, UV-resistant, opaque, translucent, transparent, chemically inert, medication-compatible, biocompatible, non-toxic, and/or not eliciting any undesirable local or systemic effects in the patient, etc. The barrier material can be metallic, polymeric, co-extruded, laminated, labeled, printed, printable, non-printable, writeable, non-writable, blank, textured, smooth, and/or colored.

Suitable barrier materials can include any one of or effective combination of: metal foils, metalized polyfoils, composite foils, and/or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, OPP (oriented polypropylene), PPP (polypropylene), BOPP (biaxially-oriented polypropylene), CPP (cast polypropylene), VMCPP (metallized cast polypropylene), LDPE (low density polyethylene), LLDPE (linear low density polyethylene), EVA (ethylene-vinyl acetate), PET (polyethylene terephthalate), paper, aluminum, nylon, polyester, mylar, Barex®, rubber-modified, acrylonitrile/methylacrylate copolymer, and/or polyacrylontrile copolymer resin, such as those materials available from Polynova of Richmond, British Columbia, Canada, BP Chemicals, Inc., Cleveland, Ohio, and/or Apple Converting of Oneonta, N.Y.

Any utilized barrier material, such as barrier 1200 and/or barrier portion 1205, 1210, and/or 1220 can be provided and/or packaged pre-attached to patch 1100, unattached but with patch 1100, and/or separately from (and thus unattached to) patch 1100. When provided unattached, the barrier material can be attached to patch 1100 by the patient and/or caregiver prior to application to skin 1300, or can be simply inserted and/or positioned between patch 1100 and skin 1300 (e.g., without first attaching barrier 1200 to patch 1100). The barrier material can be provided as a solid sheet that can be manually cut to a desired size.

A sheet of barrier material, which potentially is mated and/or nondestructively releasably attached to a barrier backing, can be printed, labeled, marked, pre-cut, and/or perforated to define barrier portions 1205, 1210, 1220 having predetermined shapes, such as ovals, circles, rectangles, squares, hexagons, and/or any shape configured to minimize the potential for unintentionally tearing that barrier portion.

Any of barrier portions 1205, 1210, 1220, can be provided with one or more non-destructively removable barrier backings and/or grips configured to allow that portion to be easily manually grasped and separated from delivery face 1170, skin 1300, and/or the remainder of barrier 1200.

Any barrier 1200 and/or barrier portion 1205, 1210, and/or 1220 can include a string, flag, tab 1280, and/or other indicator that potentially extends beyond and/or outside patch 1100 and/or is sized, shaped, printed, labeled, colored, textured, and/or patterned, etc. to indicate the type and/or size of barrier and/or percentage of medication delivery reduction provided.

The barrier material can have a thickness sufficient to control and/or block delivery of the medication from the portion of the patch 1100 that is covered by barrier 1200 and/or barrier portion 1205, even when patch 1100 utilizes micro-needles to deliver the medication. For example, the barrier material can have a thickness of about 0.0005 inch to about 0.1 inch (including all real number values and subranges therebetween).

Medications can include nicotine, opioids, heroin, fentanyl, methadone, cocaine, caffeine, buprenorphine, morphine, buspirone, hormones, such as estrogen, progestin, estradiol, and/or testosterone, nitroglycerin, scopolamine, clonidine, selegiline, methylphenidate, vitamin B12, 5-Hydroxytryptophan (5-HTP), rivastigmine, pramipexole, propentofylline, rotigotine, and/or chiral drugs, for example, ceftriaxone, thalidomide, propranolol, ibuprofen, ketoprofen, naproxen, peroxetine, finasteride, sertraline, paclitaxel, terfenadine, verapamil, enalapril, lisinopril, ifosamide, methyldopa, indacrinone, bupivacaine, loxiglumide, amlodipine, pyridinium, levoslmedan, ondansetron, salmeterol, ketorolac, doxazosin, cisapride, albuterol, oxybutynin, selective serotonin reuptake inhibitors such as fluoxetine, loratadine, fexofenadine, cetirizine, formoterol, triptans such as sumatriptan, doxazosin, zolpidem, sibutramine, atorvastatin, nadolol, abacavir, citalopram, nifedipine, glitazones such as troglitazone, progliotazone, and rosiglitazone, clorazepate, lorazepam, oxazepam, temazepam, omeprazole, levofloxacrn, captopril, and diltiazem.

More generally, medications can include therapeutic agents in any and all of the therapeutic areas including, but not limited to: narcotics, addictive drugs, antibiotics (including antimicrobial s, antibacterial s, antimycobacterials, antimalerials, antiamebics, anthelminics, antifungal s, and antiviral s), neoplastic agents, agents affecting the immune response (including steroidal and non-steroidal anti-inflammatory agents), blood calcium regulators, peptide and protein hormones, agents useful in glucose regulation, antithrombotics and hemostatics, antihyperlipidemic agents, thyromimetic and antithyroid drugs, antiulcer agents, histamine receptor agonists and antagonists, inhibitors of allergic response, local anesthetics, analgesics and analgesic combinations, antipsychotics, anti-anxiety agents, antidepressants agents, anorexigenics, bone-active agents, diagnostic agents, and a mixture thereof. Additional examples include: antidiarrheals, antimigraine preparations, antimotion sickness agents, antinauseants, antiparkinsonism drugs, antipruritics, antipyretics, antispasmodics (including gastrointestinal, urinary, skeletal, and smooth-muscle), anticholinergics, sympathomimetics, xanthine derivatives, cardiovascular preparations (including calcium channel blockers, beta-blockers, antiarrythmics, antihypertensives, diuretics, vasodilators including general coronary, peripheral and cerebral), central nervous system stimulants including cough and cold preparations, decongestants, diagnostics, hormones, immunosuppressives, parasympatholytics, parasympathomimetics, sedatives, tranquilizers, and/or mixtures thereof.

Stated differently, the term "medication" as used herein is intended to have the broadest reasonable meaning, and can be used interchangeably with "drug", "active agent", "pharmaceutical", "medicament", and/or any phrase indicating a composition of matter intended to provide a beneficial effect including a therapeutic, prophylactic, pharmacological, and/or physiological substance, cosmetic and/or personal care preparations, and/or combinations and/or mixtures thereof. More specifically, any substance that is capable of producing a pharmacological response, localized and/or systemic, irrespective of whether therapeutic, diagnostic, cosmetic, and/or prophylactic in nature. It should be noted that the active agents can be used singularly and/or in combinations and/or mixtures. There is no limitation on the type of active agent that can be used. The medication can be in different forms depending on the solubility, flux, and/or release characteristics desired, such as neutral molecules, components of molecular complexes, and/or pharmaceutically acceptable salts, free acids, and/or bases, and/or quaternary salts of the same. Simple derivatives of the medications such as pharmaceutically acceptable ethers, esters, amides, and the like that have desirable retention and/or release characteristics but which are easily metabolized at body pH, and/or enzymes, pro-active forms, pro-drugs, and/or the like, also can be employed.

It should be appreciated that one or more of these and other medications described herein can exist in many pharmaceutically acceptable salts. Examples of such salts include those generated by using inorganic agents (i.e., inorganic cations such as sodium, potassium, calcium, etc., and/or inorganic anions such as chloride, bromide, etc.) and/or organic agents (i.e., organic cations such as piperazinyl, triazinyl, etc., and/or organic anions such as citrates, tartarates, tosylates, etc). In addition, these medications also can be present as polymorphs and/or isomers. Examples of polymorphs include monohydrates, dihydrates, hemi-hydrates, etc., as well those high-melting and low-melting polymorphs. These polymorphs can be characterized using X-ray crystallographic techniques and/or other well-known techniques in the art. Examples of isomers include geometric and optical isomers. Further, the pharmaceutical art has recognized that such salts, isomers, and polymorphs, as well as prodrugs, analogs, and metabolites for these drugs can be therapeutically effective as well and/or can be substituted with ease.

It also should be recognized that the term "medication" as used herein refers to practically any chemical substance that has pharmacological activity and/or biological activity, as well as those substances that can be used for diagnostic and/or cosmetic purposes. Thus, vitamins, such as vitamin A, C, E, K, and/or various B complexes, veterinary drugs, and/or cosmetic agents, such as wrinkle-reducing agents (including anti-oxidants, for example, ascorbic acid, ascorbyl palmitate, catechins, an polyphenol compounds), depilating agents (including calcium salt, thioglycolic acid, and/or calcium hydroxide), hair-growing agents (including relaxin, cyproterone acetate, spironolactor, flutamide, and/or minoxidil), depigmenting agents (including sulfites, bisulfites, and/or metabisulfites, and/or alkaline earth and/or alkaline earth metal compounds thereof), are also included. Further, the term "medication" includes peptides, proteins, carbohydrates, fats, etc. that are known to exert biological and/or pharmacological effects.

A sealable container (e.g., bag, envelop, or pouch, etc.) 1500 can be provided with patch 1100 and/or barrier 1200 to allow for safe disposal of a new or used patch 1100 (with or without barrier 1200 attached thereto) by placing the patch 1100 within the container and then sealing the container, such as via a sliding zipper, adhesive, and/or other container sealing mechanism.

Figure 12:
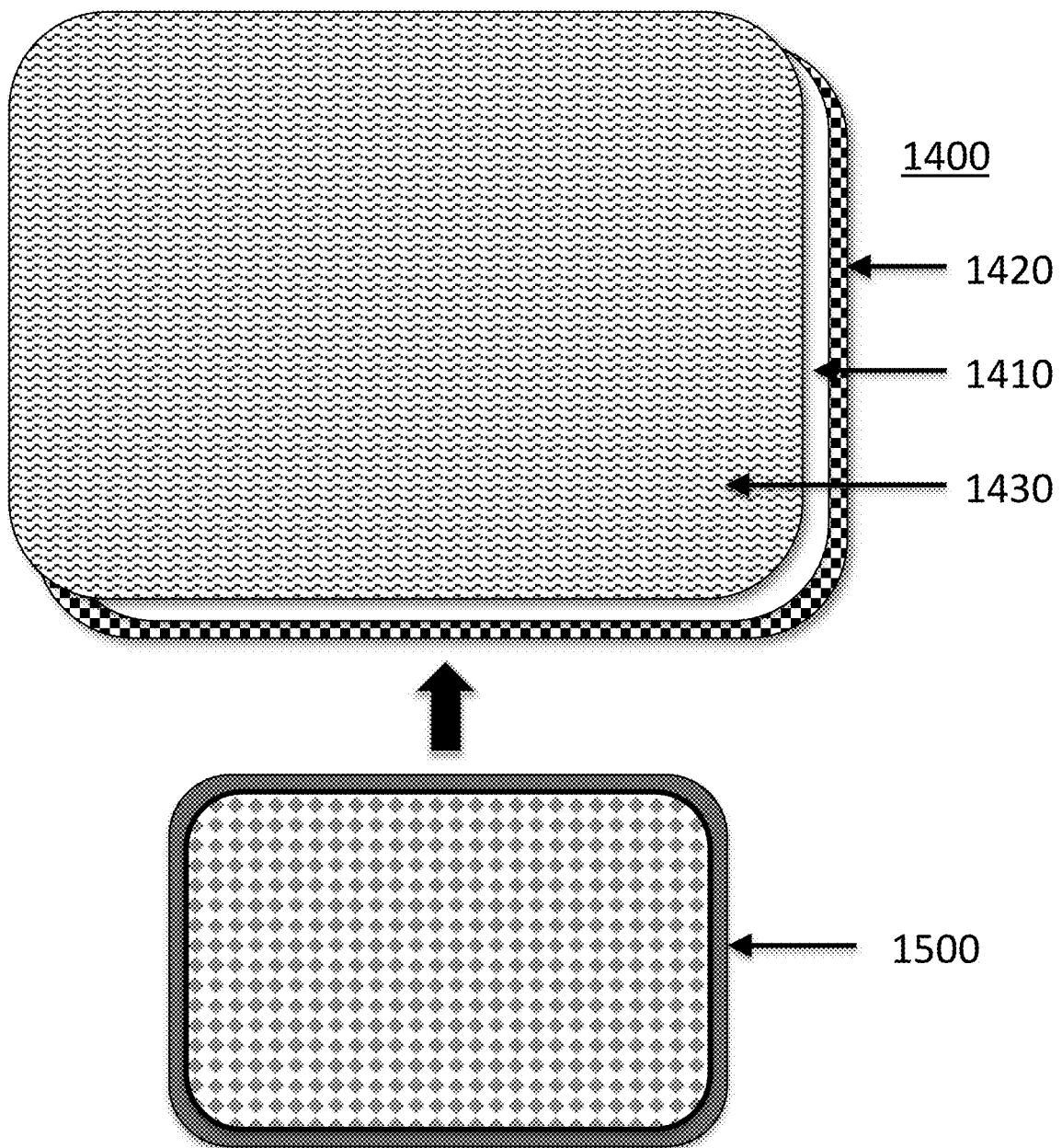
FIG. 12 is a side view of an exemplary embodiment of a system.

FIG. 12 is a side and/or perspective view of an exemplary embodiment of system 1000, showing a sealable container (e.g., bag, envelop, or pouch, etc.) 1500 that can be included with a patch and/or barrier to allow for safe disposal of a used patch 1500 (with or without a barrier attached thereto) by placing the used patch 1500 within container 1400 and then sealing the container 1400, such as via a sliding zipper, adhesive, and/or other container sealing mechanism. For example, a sealable container can include a top 1430, a bottom 1410, and an adhesive strip 1420 attached to, e.g., bottom 1410. Once a used patch 1500 is inserted into container 1400 before it is sealed, adhesive strip 1420 can be exposed to allow top 1430 to seal to bottom 1410, thereby sealing container 1400. Note that the sealable container can be provided with a patch or barrier, potentially being non-destructably removably attached to a patch or barrier and then removed prior to their use. U.S. Pat. No. 8,623,404 is incorporated herein by reference in its entirety and for its discussion of transdermal patch pouches.

Each of the following patent publications is incorporated herein by reference in its entirety and for its discussion of, as relevant, transdermal patches, barriers, backings, adhesives, containers, sealing mechanisms, medications, materials, and/or configurations: EPO 559411A1, U.S. Pat. Nos. 5,473,966, 5,733,571, 5,804,215, 8,784,880, and 9,289,397, and International Patent Applications WO2001068062A2, WO2017125455A1, and WO2018231219A1.

Certain exemplary embodiments provide a system for controlling delivery of a transdermally-delivered medication, comprising:
  a flux controller that is configured to control a delivery flowrate of the medication to skin of a patient from a delivery face of a skin-attachable transdermal patch;
  the patch; and/or
  a substantially impermeable envelope configured to sealingly contain the patch and the flux controller,
  wherein:
    the flux controller defines a substantially impermeable portion having a plurality of apertures therethrough;
    each of the plurality of apertures is sized to allow the medication to permeate therethrough from the patch to the skin;
    the plurality of apertures defines a predetermined reduction in a labeled medication flowrate for the patch;
    the plurality of apertures are dispersed in a predetermined pattern;
    the plurality of apertures are dispersed in a random pattern;
    the plurality of apertures are dispersed in an array;
    the flux controller is non-destructively removeably adhered to a backing;
    the flux controller is configured to be non-destructively removed, from a backing to which it is adhered, prior to being paired with the patch;
    the patch is configured to be attached to the skin;
    the flux controller is configured to be attached to the skin;
    the flux controller is configured as a semi-permeable tape having adhesive attached thereto;
    further the flux controller is configured as a semi-permeable tape having a skin-adhering adhesive attached thereto; and/or the flux controller is configured as a semi-permeable tape having a patch-adhering adhesive attached thereto.

Certain exemplary embodiments provide a system for controlling delivery of a transdermally-delivered medication, comprising:
  a flux controller that is configured to control a delivery flowrate of the medication to skin of a patient from a delivery face of a skin-attachable transdermal patch;
  the patch; and/or
  a substantially impermeable envelope configured to sealingly contain the patch and the flux controller;
  wherein:
    the flux controller defines a substantially impermeable portion having a plurality of apertures therethrough;
    each of the plurality of apertures is sized to allow the medication to permeate therethrough from the patch to the skin; and
    the plurality of apertures defines a predetermined reduction in a labeled medication flowrate for the patch.
    the plurality of apertures are dispersed in a predetermined pattern;
    the plurality of apertures are dispersed in a random pattern;
    the plurality of apertures are dispersed in an array;
    the flux controller is non-destructively removeably adhered to a backing;
    the flux controller is configured to be non-destructively removed, from a backing to which it is adhered, prior to being paired with the patch;
    the patch is configured to be attached to the skin;
    the flux controller is configured to be attached to the skin;
    the flux controller is configured as a semi-permeable tape having adhesive attached thereto;
    the flux controller is configured as a semi-permeable tape having a skin-adhering adhesive attached thereto; and/or
    the flux controller is configured as a semi-permeable tape having a patch-adhering adhesive attached thereto.

Certain exemplary embodiments provide a system for controlling delivery of a system for controlling delivery of a transdermally-delivered medication, comprising:
  a flux controller that is configured to control a delivery flowrate of the medication to skin of a patient from a delivery face of a skin-attachable transdermal patch;
  wherein:
    the flux controller defines an adjustably-sizable aperture configured to be manually sized to allow the medication to permeate therethrough from the patch to the skin at an adjustable fraction of a labeled medication flowrate for the patch.

Definitions

When the following phrases are used substantively herein, the accompanying definitions apply. These phrases and definitions are presented without prejudice, and, consistent with the application, the right to redefine these phrases via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

a—at least one.
  about—around and/or approximately.
  above—at a higher level.

across—from one side to another.

activity—an action, act, step, and/or process or portion thereof.

adapt—to design, make, set up, arrange, shape, configure, and/or make suitable and/or fit for a specific purpose, function, use, and/or situation.

adapter—a device used to effect operative compatibility between different parts of one or more pieces of an apparatus or system.

adhere—to make stick, bond, cling, cleave, hold, stick fast to something, stay attached, and/or resist separation.

adhesive—a substance that adheres to a surface and/or causes adherence between surfaces.

adjust—to move and/or change (something) so as to conform with something else and/or to be in a suitable and/or more effective arrangement and/or desired condition.

adjustable—configured to change, match, and/or fit.

after—following in time and/or subsequent to.

allow—to provide, let do, happen, and/or permit.

along—through, on, beside, over, in line with, and/or parallel to the length and/or direction of; and/or from one end to the other of.

and—in conjuction with.

and/or—either in conjunction with or in alternative to.

any—one, some, every, and/or all without specification.

aperture—an opening, hole, gap, passage, and/or slit.

apparatus—an appliance or device for a particular purpose.

approximately—about and/or nearly the same as.

area—the measure of the space within a closed 2-dimensional region.

around—about, surrounding, and/or on substantially all sides of; and/or approximately.

array—a matrix, table, and or arrangement of multiple units, usually ordered, whereby the array can be organized in linear, flat, or 3-dimensional positioning of the multiple units.

as long as—if and/or since.

associate—to join, connect together, and/or relate.

at—in, on, and/or near.

at least—not less than, and possibly more than.

attached—joined or secured together.

axis—a straight line about which a body and/or geometric object rotates and/or can be conceived to rotate and/or a center line to which parts of a structure and/or body can be referred.

backing—something that covers, forms, lines, protects, supports, reinforces, and/or strengthens the back of something.

based on—indicating one or more factors that affect a determination, but not necessarily foreclosing additional factors that might affect that determination.

be—to exist in actuality.

between—in a separating interval and/or intermediate to.

by—via and/or with the use and/or help of.

can—is capable of, in at least some embodiments.

cause—to bring about, provoke, precipitate, produce, elicit, be the reason for, result in, and/or effect.

circuit—an electrically conductive pathway and/or a communications connection established across two or more switching devices comprised by a network and between corresponding end systems connected to, but not comprised by the network.

composition of matter—a combination, reaction product, compound, mixture, formulation, material, and/or composite formed by a human and/or automation from two or more substances and/or elements.

comprising—including but not limited to.

conceive—to imagine, conceptualize, form, and/or develop in the mind.

concentration—a measure of how much of a given substance is mixed, dissolved, contained, and/or otherwise present in and/or with another substance, and/or a measure of the amount of dissolved substance contained per unit of volume and/or the amount of a specified substance in a unit amount of another substance, both measures defining a structure of a composition that comprises both substances.

configure—to design, arrange, set up, shape, and/or make suitable and/or fit for a specific purpose, function, use, and/or situation.

configured to—designed, arranged, set up, shaped, and/or made suitable and/or fit for a specific purpose, function, use, and/or situation, and/or having a structure that, during operation, will perform the indicated activity(ies). To the extent relevant to the current application, the use of "configured to" is expressly not intended to invoke 35 U.S.C. § 112(f) for that structure.

connect—to join or fasten together.

contain—to restrain, hold, and/or keep within limits.

containing—including but not limited to.

control—to exercise authoritative and/or dominating influence over, cause to act in a predetermined manner, direct, adjust to a requirement, and/or regulate.

controller—a device used to control a property, characteristic, behavior, and/or effect of another device.

convert—to transform, adapt, and/or change.

corresponding—related, associated, accompanying, similar in purpose and/or position, conforming in every respect, and/or equivalent and/or agreeing in amount, quantity, magnitude, quality, and/or degree.

coupleable—capable of being joined, connected, and/or linked together.

coupling—linking in some fashion.

create—to bring into being.

define—to establish the meaning, relationship, outline, form, and/or structure of; and/or to precisely and/or distinctly describe and/or specify.

delivery—an act of conveying and/or transferring.

derive—to receive, obtain, and/or produce from a source and/or origin.

determine—to find out, obtain, calculate, decide, deduce, ascertain, and/or come to a decision, typically by investigation, reasoning, and/or calculation.

device—a machine, manufacture, and/or collection thereof.

disperse—to scatter, strew, separate, drive off, move, and/or distribute widely and/or in different directions.

each—every one of a group considered individually.

effective—sufficient to bring about, provoke, elicit, and/or cause.

embodiment—an implementation, manifestation, and/or concrete representation.

envelope—a bag, covering, enclosure, and/or wrapping.

estimate—(n) a calculated value approximating an actual value; (v) to calculate and/or determine approximately and/or tentatively.

exemplary—serving as an example, instance, and/or illustration.

first—a label for a referenced element in one or more patent claims, but that label does not necessarily imply any type of ordering to how that element (or any other elements of a similar type) is implemented in embodiments of the claimed subject matter.

flow—(n) a stream, current, and/or continuous transference; (v) to move and/or run smoothly with unbroken continuity, as in the manner characteristic of a fluid.

flowrate—the amount of fluid that flows in a given time and/or a rate at which a unit of a flow passes a given point in a predetermined period of time.

flux—a flowrate and/or rate of flow of a fluid.

for—with a purpose of.

fraction—a part and/or portion of a whole and/or entirety.

from—used to indicate a source, origin, and/or location thereof.

further—in addition.

further—in addition.

generate—to create, produce, give rise to, and/or bring into existence.

given— having—possessing, characterized by, comprising, and/or including, but not limited to.

impermeable—impervious, configured to prevent fluids (especially liquids) to pass and/or diffuse through, and/or not permeable.

including—including but not limited to.

initialize—to prepare something for use and/or some future event.

install—to connect or set in position and prepare for use.

into—to a condition, state, or form of.

is—to exist in actuality.

label—(n) an item used to identify something and/or someone, as a small piece of paper and/or cloth attached to an article to designate its origin, owner, contents, use, and/or destination; (v) to attach a label to and/or to designate and/or describe by and/or on a label.

layer—a ply, strata, sheet, and/or single thickness of a material configured to cover a surface.

longitudinal—of and/or relating to a length; placed and/or running lengthwise.

longitudinal axis—a straight line defined parallel to an object's length and passing through a centroid of the object.

manage—to exert control and/or influence over, direct, and/or control the use, affairs, and/or interests of.

manually—employing human rather than mechanical energy.

may—is allowed and/or permitted to, in at least some embodiments.

medication—a substance adapted to relieve at least one symptom of and/or cure a medical condition.

method—one or more acts that are performed upon subject matter to be transformed to a different state or thing and/or are tied to a particular apparatus, said one or more acts not a fundamental principal and not pre-empting all uses of a fundamental principal.

microgram—one one-millionth of a gram.

milligram—one one-thousandth of a gram.

mix—to combine and/or blend into one mass, stream, and/or mixture.

molecule—the smallest particle of a substance that retains the chemical and physical properties of the substance and is composed of two or more atoms; and/or a group of like or different atoms held together by chemical forces.

near—a distance of less than approximately [X].

no—an absence of and/or lacking any.

non-destructively—to perform substantially without damaging.

one—being and/or amounting to a single unit, individual, and/or entire thing, item, and/or object.

operable—practicable and/or fit, ready, and/or configured to be put into its intended use and/or service.

operative—when in operation for its intended use and/or service.

or—a conjunction used to indicate alternatives, typically appearing only before the last item in a group of alternative items.

outside—beyond a range, boundary, and/or limit; and/or not within.

pair—(n) a quantity of two of something and/or two things that are matched for use together; (v) to combine and/or join (one person and/or thing) with another to form a pair.

parallel—of, relating to, and/or designating lines, curves, planes, and/or surfaces everywhere equidistant.

patch—a covering configured to be applied to the skin.

patient—one who is scheduled to receive, has been admitted to receive, or has received, health care, and/or a human or other type of animal under supervision for health care purposes.

pattern—a characteristic form and/or arrangement.

per—for each and/or by means of.

permeate—to penetrate, flow through, be absorbed through, pervade, and/or pass through the openings and/or interstices of.

perpendicular—intersecting at or forming substantially right angles.

plurality—the state of being plural and/or more than one.

portion—a part, component, section, percentage, ratio, and/or quantity that is less than a larger whole.

pre-—a prefix that precedes an activity that has occurred beforehand and/or in advance.

predetermine—to determine, decide, and/or establish in advance.

prevent—to hinder, avert, and/or keep from occurring.

prior—before and/or preceding in time or order.

probability—a quantitative representation of a likelihood of an occurrence.

product—something produced by human and/or mechanical effort.

project—to calculate, estimate, or predict.

provide—to furnish, supply, give, and/or make available.

random—selected in a substantially unbiased manner within a predetermined range.

range—a measure of an extent of a set of values and/or an amount and/or extent of variation.

ratio—a relationship between two quantities expressed as a quotient of one divided by the other.

receive—to get as a signal, take, acquire, and/or obtain.

recommend—to suggest, praise, commend, and/or endorse.

reduce—to make and/or become lesser and/or smaller.

reduction—a diminishment in magnitude.

removably—configured to be removed.

remove—to eliminate, remove, and/or delete, and/or to move from a place and/or position occupied.

repeat—to do again and/or perform again.

repeatedly—again and again; repetitively.

request—to express a desire for and/or ask for.

result—(n.) an outcome and/or consequence of a particular action, operation, and/or course; (v.) to cause an outcome and/or consequence of a particular action, operation, and/or course.

said—when used in a system or device claim, an article indicating a subsequent claim term that has been previously introduced.

seal—to shut close, keep closed, make fast, keep secure, and/or prevent leakage.

second—a label for an element in one or more patent claims, the element other than a "first" referenced element of a similar type, but the label does not necessarily imply any type of ordering to how that "second" element or the "first" element is implemented in embodiments of the claimed subject matter.

select—to make a choice or selection from alternatives.

semi-permeable—partially permeable and/or allowing passage of a portion of.

set—a related plurality.

size—(v) to make, cut, and/or shape to a required size; (n) the physical dimensions, proportions, magnitude, amount, and/or extent of an entity.

skin—the membranous tissue forming the external covering of an animal and consisting in vertebrates of the epidermis and dermis.

skin-attachable—configured (such as via adhesive) to be attached to skin.

species—a class of individuals and/or objects grouped by virtue of their common attributes and assigned a common name; a division subordinate to a genus.

store—to place, hold, and/or retain data, typically in a memory.

substantially—to a considerable, large, and/or great, but not necessarily whole and/or entire, extent and/or degree.

support—to bear the weight of, especially from below.

system—a collection of mechanisms, devices, machines, articles of manufacture, processes, data, and/or instructions, the collection designed to perform one or more specific functions.

tape—a continuous narrow, flexible strip of cloth, metal, paper, and/or plastic, having an adhesive surface.

that—used as the subject or object of a relative clause.

therapeutically effective—an amount of medication that is sufficient to achieve the desired local or systemic effect or result, such as to prevent, cure, diagnose, mitigate or treat a disease or condition, when applied topically over the duration of intended use.

therethrough—in one end and out another end of an object.

thereto—to that.

through—across, among, between, and/or in one side and out the opposite and/or another side of.

to—a preposition adapted for use for expressing purpose.

transdermal—absorbed through and/or by way of the unbroken skin, and often referring to medications applied in time-release forms (skin patches).

transform—to change in measurable: form, appearance, nature, and/or character.

transmit—to send as a signal, provide, furnish, and/or supply.

treatment—an act, manner, or method of handling and/or dealing with someone and/or something.

upon—immediately or very soon after; and/or on the occasion of.

use—to put into service.

via—by way of and/or utilizing.

weight—a force with which a body is attracted to Earth or another celestial body, equal to the product of the object's mass and the acceleration of gravity; and/or a factor and/or value assigned to a number in a computation, such as in determining an average, to make the number's effect on the computation reflect its importance, significance, preference, impact, etc.

when—at a time and/or during the time at which.

wherein—in regard to which; and; and/or in addition to.

which—a pronoun adapted to be used in clauses to represent a specified antecedent; and/or what particular one or ones.

with—accompanied by.

with regard to—about, regarding, relative to, and/or in relation to.

with respect to—about, regarding, relative to, and/or in relation to.

within—inside the limits of.

zone—a region and/or volume having at least one predetermined boundary.

Note

Various substantially and specifically practical and useful exemplary embodiments of the claimed subject matter are described herein, textually and/or graphically, including the best mode, if any, known to the inventor(s), for implementing the claimed subject matter by persons having ordinary skill in the art. References herein to "in one embodiment", "in an embodiment", or the like do not necessarily refer to the same embodiment.

Any of numerous possible variations (e.g., modifications, augmentations, embellishments, refinements, and/or enhancements, etc.), details (e.g., species, aspects, nuances, and/or elaborations, etc.), and/or equivalents (e.g., substitutions, replacements, combinations, and/or alternatives, etc.) of one or more embodiments described herein might become apparent upon reading this document to a person having ordinary skill in the art, relying upon his/her expertise and/or knowledge of the entirety of the art and without exercising undue experimentation. The inventor(s) expects any person having ordinary skill in the art, after obtaining authorization from the inventor(s), to implement such variations, details, and/or equivalents as appropriate, and the inventor(s) therefore intends for the claimed subject matter to be practiced other than as specifically described herein. Accordingly, as permitted by law, the claimed subject matter includes and covers all variations, details, and equivalents of that claimed subject matter. Moreover, as permitted by law, every combination of the herein described characteristics, functions, activities, substances, and/or structural elements, and all possible variations, details, and equivalents thereof, is encompassed by the claimed subject matter unless otherwise clearly indicated herein, clearly and specifically disclaimed, or otherwise clearly unsuitable, inoperable, or contradicted by context.

The use of any and all examples, or exemplary language (e.g., "such as") provided herein, is intended merely to better illuminate one or more embodiments and does not pose a limitation on the scope of any claimed subject matter unless otherwise stated. No language herein should be construed as indicating any non-claimed subject matter as essential to the practice of the claimed subject matter.

Thus, regardless of the content of any portion (e.g., title, field, background, summary, description, abstract, drawing figure, etc.) of this document, unless clearly specified to the contrary, such as via explicit definition, assertion, or argument, or clearly contradicted by context, with respect to any claim, whether of this document and/or any claim of any document claiming priority hereto, and whether originally presented or otherwise:

there is no requirement for the inclusion of any particular described characteristic, function, activity, substance, or structural element, for any particular sequence of activities, for any particular combination of substances, or for any particular interrelationship of elements;

no described characteristic, function, activity, substance, or structural element is "essential"; and within, among, and between any described embodiments:
any two or more described substances can be mixed, combined, reacted, separated, and/or segregated;
any described characteristic, function, activity, substance, component, and/or structural element, or any combination thereof, can be specifically included, duplicated, excluded, combined, reordered, reconfigured, integrated, and/or segregated;
any described interrelationship, sequence, and/or dependence between any described characteristics, functions, activities, substances, components, and/or structural elements can be omitted, changed, varied, and/or reordered;
any described activity can be performed manually, semi-automatically, and/or automatically;
any described activity can be repeated, performed by multiple entities, and/or performed in multiple jurisdictions.

The use of the terms "a", "an", "said", "the", and/or similar referents in the context of describing various embodiments (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

When any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values therebetween, such as for example, 1.1, 2.5, 3.335, 5, 6.179, 8.9999, etc., and includes all sub-ranges therebetween, such as for example, 1 to 3.65, 2.8 to 8.14, 1.93 to 9, etc., even if those specific values or specific sub-ranges are not explicitly stated.

When any phrase (i.e., one or more words) appearing in a claim is followed by a drawing element number, that drawing element number is exemplary and non-limiting on claim scope.

No claim or claim element of this document is intended to invoke 35 USC 112(f) unless the precise phrase "means for" is followed by a gerund.

Any information in any material (e.g., a United States patent, United States patent application, book, article, web page, etc.) that has been incorporated by reference herein, is incorporated by reference herein in its entirety to its fullest enabling extent permitted by law yet only to the extent that no conflict exists between such information and the other definitions, statements, and/or drawings set forth herein. In the event of such conflict, including a conflict that would render invalid any claim herein or seeking priority hereto, then any such conflicting information in such material is specifically not incorporated by reference herein. Any specific information in any portion of any material that has been incorporated by reference herein that identifies, criticizes, or compares to any prior art is not incorporated by reference herein.

Applicant intends that each claim presented herein and at any point during the prosecution of this application, and in any application that claims priority hereto, defines a distinct patentable invention and that the scope of that invention must change commensurately if and as the scope of that claim changes during its prosecution. Thus, within this document, and during prosecution of any patent application related hereto, any reference to any claimed subject matter is intended to reference the precise language of the then-pending claimed subject matter at that particular point in time only.

Accordingly, every portion (e.g., title, field, background, summary, description, abstract, drawing figure, etc.) of this document, other than the claims themselves and any provided definitions of the phrases used therein, is to be regarded as illustrative in nature, and not as restrictive. The scope of subject matter protected by any claim of any patent that issues based on this document is defined and limited only by the precise language of that claim (and all legal equivalents thereof) and any provided definition of any phrase used in that claim, as informed by the context of this document when reasonably interpreted by a person having ordinary skill in the relevant art.

What is claimed is:

1. A system for manually controlling delivery of a transdermally-delivered medication, comprising:
   a transdermal patch defining a delivery face, the transdermal patch configured to deliver medication to the skin of a patient; and
   a flux controller that is configured for the patient to selectively manually control a delivery flowrate of the medication to the skin of the patient from the delivery face of the transdermal patch;
   wherein:
      the flux controller defines at least one selectively patient-sizable medication-impermeable portion configured to define a predetermined reduction in a labeled medication flowrate for the transdermal patch; and
      the flux controller is configured to be located between the skin and a portion of the transdermal patch.

2. The system of claim 1, further comprising:
   a medication-impermeable envelope configured to sealingly contain the transdermal patch and the flux controller.

3. The system of claim 1, wherein:
   the flux controller is non-destructively removeably adhered to a backing.

4. The system of claim 1, wherein:
   the flux controller is configured to be non-destructively manually removed by the patient from the backing prior to being paired by the patient with the transdermal patch.

5. The system of claim 1, wherein:
   the transdermal patch is configured to be attached to the skin.

6. The system of claim 1, wherein:
   the flux controller has a skin-adhering adhesive attached thereto.

7. The system of claim 1, wherein:
   the flux controller has a transdermal patch-adhering adhesive attached thereto.

8. A system for manually controlling delivery of a transdermally-delivered medication from a transdermal patch that defines a delivery face, the transdermal patch configured to deliver medication to the skin of a patient, the system comprising:

a flux controller that is configured for the patient to selectively manually control a delivery flowrate of the medication to the skin of the patient from the delivery face of the transdermal patch;

wherein:

the flux controller defines a plurality of medication-permeable apertures therethrough that are configured to define a predetermined reduction in a labeled medication flowrate for the transdermal patch.

9. The system of claim 8, wherein:
the flux controller is non-destructively removeably adhered to a backing.

10. The system of claim 8, wherein:
the flux controller is configured to be non-destructively removed, from a backing to which it is adhered, prior to being paired with the transdermal patch.

11. The system of claim 8, wherein:
the transdermal patch is configured to be attached to the skin.

12. The system of claim 8, wherein:
the flux controller is configured to be attached to the skin.

13. The system of claim 8, wherein:
the flux controller is configured as a medication-impermeable layer that defines the plurality of medication-permeable aperatures, the plurality of medication-permeable apertures extending through the medication-impermeable layer.

14. The system of claim 8, wherein:
the flux controller is configured as a medication-impermeable layer that defines the plurality of medication-permeable aperatures, the plurality of medication-permeable apertures extending through the medication-impermeable layer, the plurality of medication-permeable aperatures distributed uniformly across the medication-impermeable layer.

15. The system of claim 8, wherein:
the flux controller is configured as a medication-impermeable layer having a transdermal patch-adhering adhesive attached thereto.

16. The system of claim 8, wherein:
the flux controller comprises at least one manually-graspable barrier grip.

17. The system of claim 8, wherein:
the flux controller is configured for the patient to selectively manually control the delivery flowrate of the medication to the skin of the patient from the delivery face of the transdermal patch, the delivery face utilizing microneedles to deliver the medication.

18. The system of claim 8, wherein:
the flux controller defines a non-textual indicia that correlates to the flux controller's medication delivery reduction.

19. The system of claim 8, further comprising:
the transdermal patch.

20. The system of claim 8, further comprising:
a medication-impermeable envelope configured to sealingly contain the transdermal patch and the flux controller.

* * * * *